(12) United States Patent
Cremer et al.

(10) Patent No.: US 6,197,501 B1
(45) Date of Patent: *Mar. 6, 2001

(54) ARRANGEMENT OF NUCLEIC ACID SEQUENCES FOR COMPARATIVE GENOMIC HYBRIDIZATION

(75) Inventors: Thomas Cremer; Thomas Ried; Michael Speicher, all of Heidelberg; Anna Jauch, Heddesheim; Peter Lichter, Gaiberg, all of (DE)

(73) Assignee: Deutsches Krebsforschungszentrum, Heidelberg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/669,229

(22) Filed: Jun. 24, 1996

(30) Foreign Application Priority Data

Dec. 27, 1993 (DE) ................................. 43 44 726

(51) Int. Cl.⁷ ............................. C12Q 1/68; C12P 19/34; C07H 21/02
(52) U.S. Cl. ................................ 435/6; 435/5; 435/91.2; 536/23.1; 536/24.3; 536/24.31; 536/24.32; 536/24.33
(58) Field of Search .................... 435/5, 6, 91.2; 536/24.3, 24.31, 24.32, 24.33

(56) References Cited

U.S. PATENT DOCUMENTS 5,665,549 * 9/1997 Pinkel et al. ............................ 435/6
5,690,894 * 11/1997 Pinkel et al. ......................... 422/68.1

FOREIGN PATENT DOCUMENTS

WO 93/21345 10/1993 (WO).
WO 93/18186 9/1996 (WO).

OTHER PUBLICATIONS

Ng et al, "Methods for analysis of multiple cystic fibrosis mutations", Hum. Genet. 87:613–617, 1991.*
Bentz et al, "Comparative genomic hybridization in the investigation of myeloid leukemias", Genes Chromosomes Cancer 12:193–200, 1995.*
Speicher et al, "Correlation of microscopic phenotype with genotype in a formalin fixed, paraffin embedded testicular germ cell tumor with universal DNA amplification, comparative genomic hybridization and interphase cytogenics", Am. J. Pathology 146(6) Jun. 1995.*
"Oncogene Amplification", *Seminars in Cancer Biology*, Feb. 1993.
O.P. Kallioniemi et al., "Comparqative Genomic Hybridization: A Rapid New Method for Detecting and Mapping DNA Amplification in Tumors", *Seminars in Cancer Biology*, vol. 4, 1993:pp. 41 –46.
S. Du Manoir et al. "Detection of Complete and Partial Chromosome Gains and Losses by Comparative Genomic in Situ Hybridization", *Human Genetics* (1993) 90: 590 –610.
Dudin et al, "Sorting of chromosomes by magnetic seperation", Human Genetics 80:111–116, 1988.*
Slim et al, "Relative order determination of four Yp cosmids on metaphase and interphase chromosomes by two–color competitive in situ hybridization", Human Genetics 88:21–26, 1991.*
Stratagene Catalog, p. 39, 1988.*

* cited by examiner

*Primary Examiner*—Jeffrey Fredman
(74) *Attorney, Agent, or Firm*—Reed Smith LLP

(57) ABSTRACT

A method of determining the relative number of nucleic acid sequences in test cells which provides for a high resolution during comparative genomic hybridization by keeping all components separate from each other and selecting target nucleic acids which have a high resolution capability for determining genomic imbalances in the test cells and which facilitate a screening of the test cells for over- or under-expression of individual genes.

3 Claims, No Drawings

ARRANGEMENT OF NUCLEIC ACID SEQUENCES FOR COMPARATIVE GENOMIC HYBRIDIZATION

BACKGROUND OF THE INVENTION

The invention relates to an arrangement of nucleic acid sequences and their use.

With methods of the comparative genomic in situ hybridization (CGH) of reference chromosome preparations of normal Karyotype, it is now possible to determine in a genomic test DNA (for example, tumor DNA, with the suspicion for the existence of unbalanced chromosome aberrations) gains and losses of genoma sections of about 10 Mbp. With amplifications, it is also possible to chart substantially smaller DNA sections by CGH on reference chromosome preparations. These methods are known from Du Manoir, S.; Speicher, M. R.; Joos, S.; Schröck, E.; Popp, S.; Döhner, H.; Kovacs, G.; Robert-Nicoud, M.; Lichier, P.; Cremer, T.; "DETECTION OF COMPLETE AND PARTIAL CHROMOSOME GAINS AND LOSSES BY COMPARATIVE GENOMIC IN SITU HYBRIDIZATION". Hum. Genet. 90:590–610, 1993 or Joos, S.; Scherthan, H.; Speicher, M. R.; Schlegel, J.; Cremer, T.; Lichter, P.; "DETECTION OF AMPLIFIED GENOMIC SEQUENCES BY REVERSE CHROMOSOME PAINTING USING GENOMIC TUMOR DNA AS PROBE"., Hum. Genet. 90: 584–589, 1993. As genomic reference-DNA, DNA may be used which, if available, can be gathered from cells with a normal chromosome complement thereof or from another person.

With today's state of the art of (CGH, there are two essential limitations. First a further increase of the resolution capability is desirable. It is expected that, with prometa phase chromosomes, CGH analyses of partial trisomy and monosomy with a resolution capability of $\geq 3$ Mbp become possible. This corresponds to an average DNA content of banded chromosomes with a high resolution chromosomal bands with about 1000 bands per haploid chromosome set. However, for many applications, a CGH test would be desirable by which gains and losses of particular genes or even intragenic DNA sections could be safely determined. It is possible that a better resolution can be achieved if the CGH analyses are performed with even more decondensed chromatin structures. On the other hand, CGH for mitotic reference chromosomes have the disadvantage that the fully automatic identification of chromosomes by fluorescence banding for example with DAPI and measurement of the CGH fluorescence quotient is complicated and time-consuming.

It is the object of the invention to provide an arrangement of nucleic acid sequences by which, with relatively little technical expenses automation and substantially improved resolution can be achieved.

SUMMARY OF THE INVENTION

A method of determining the relative number of nucleic acid sequences in test cells which provides for a high resolution during comparative genomic hybridization by keeping all components separate from each other and selecting target nucleic acids which have a high resolution capability for determining genomic imbalances in the test cells and which facilitate a screening of the test cells for over- or under-expression of individual genes.

A substantial improvement with regard to the resolution capability and also with regard to a fully automatic evaluation is achieved by a CNH-matrix test (CNH=comparative nucleic acid hybridization) wherein, in place of mitotic chromosomes, specific nucleic acid sequences (designated below as target nucleic acids, in the case of DNA as target-DNA, in the case of RNA as target RNA) are deposited on a suitable carrier material (designated below as matrix). A target nucleic acid may consist of one or many different DNA- or, respectively, RNA-sequences. The complexity of a target nucleic acid depends on the respective formulation of the question. The CNH-matrix test should facilitate a fully automatic gain or deletion balance of genetic imbalances in a genomic test-DNA wherein the resolution capability for the selected genome sections, for example, individual genes may be in the kbp-range.

The target nucleic acids are immobilized on a solid matrix which consists for example of filter paper or of glass. The area of the matrix in which a target nucleic acid is deposited is designated below as a slot. Subsequently, the simultaneous hybridization of test- and reference-DNA occurs against the target nucleic acids. Alternatively, the hybridization of test- and reference-DNA against the target nucleic acid may also be done in solution. For this, it is necessary to provide a separate hybridization for each target nucleid acid. The evaluation occurs after binding of the hybridization products on a solid matrix or directly in solution.

In contrast to the highly variable arrangement of individual chromosomes in metaphase representations as they are utilized in a comparative genomic in situ hybridization, the position of the genome sections which are to be tested for gains and losses in the test DNA can be clearly determined on a matrix. Furthermore, the sizes and shapes of individual chromosomes differ substantially from metaphase to metaphase, whereas the size and geometry of the particular slots can be standardized. These possibilities of a standardization of position, size and geometry of the target nucleic acid slots facilitate the fully automatic evaluation of a matrix in comparison to CGH of metaphase chromosomes to a great extent. Size and distance of the individual slots can be so selected that the automatic control of a table with the matrix disposed thereon or, alternatively, of a light beam can be easily realized with sufficient precision. If desired, fluorescence quotients within a slot can also be determined in several separate areas and an average can be calculated therefrom.

DESCRIPTION OF EMBODIMENTS OF THE INVENTION

The invention will be described on the basis of a CNH matrix test for the analysis of imbalances of genomic DNA or, respectively, expressed RNA in various tissues and cell types using seven examples.

For the comparative quantification of the gene expression in various tissues and cell types a test is to be developed which is based on the comparative hybridization of differently marked mRNA or, respectively, cDNA of two tissues or cell types on a matrix with the corresponding cDNA-clones.

The principle of the CNH-matrix test is based on the comparative hybridization of test and reference nucleic acid samples with respect to target samples, which were deposited on glass or on a filter, and the quantitative determination of fluorescence quotients for the hybridized samples. The individual method steps are described below:

1. Selection of test and reference DNA or, respectively, RNA samples.

Genomic test and reference DNA's are selected in accordance with the same criteria as with the CGH tests for metaphase chromosomes. It is possible to use universal genomic DNA or genomic DNA amplified by means of DOP-PCR. This is described for example by Speicher, M. R.; du Manoir, S.; Schröck, E.; Holtgreve-Grez, H.; Schoell, B.; Lengauer, C.; Cremer, T.; Ried, T.: "MOLECULAR CYTOGENETIC ANALYSIS OF FORMALIN-FIXED, PARAFFIN-EMBEDDED SOLID TUMORS BY COMPARATIVE GENOMIC HYBRIDIZATION AFTER UNIVERSAL DNA-AMPLIFICATION". Hum. Mol. Genet. 2: 1907–1914, 1993. As test and reference samples for comparative tests of the gene expression, mRNA preparations or, respectively, cDNA libraries of selected cells or tissue but also individual cDNA samples and combinations of cDNA samples can be used.

2. Selection of Target DNA or Target RNA

As target nucleic acids, which are applied to the matrix in a way described below, cloned genomic DNA sections of a species (for example, human) can be used, for example DNA preparations of plasmid clones, cosmid clones, Pi-clones, YAC-clones, which comprise genomic sections of a few kbp up to several Mbp. Instead of purified nucleic acid, sorted chromosomes or microorganisms which contain the respective target nucleic acid, can be directly applied to the matrix.

The physical mapping of the samples used should be known. For even larger genome sections such as certain chromosomal bands, mixtures of the DNA of selected genomic DNA clones can be prepared or DNA's of clone combinations can be used which are made from sorted or microdissected chromosomes of the human or other species. For comparative tests of the gene expression, cDNA samples, combinations of cDNA samples or cDNA combinations as well as mRNA fractions can be used as target nucleic acids.

Preparation of the CNH Test Matrix

The target nucleic acids needed for a desired CNH-matrix test are deposited on a filter in a geometric arrangement as desired by the tester. The arrangement may for example by such that the order of genomic target nucleic acids on the matrix from top to bottom corresponds to the order of the physical arrangement on a chromosome from $p^{th}$ to $q^{th}$. Consequently, each sample has a slot with a well defined position on the filter assigned to it. For nucleic acid bands, common paper filter can be used. For fluorescence processes the filters must be so selected that their properties such as their innate fluorescence will not disturb the detection of the fluorescence signals. In this way slots for different chromosomes, chromosome sections and genes can be arranged side-by-side in parallel columns. The selection of the target nucleic acids depends on the purpose of the diagnosis and the desired resolution capability of the CNH matrix tests. A slot matrix may contain target nucleic acids for expressed sequences or genomic sections of selected genes as well as target DNA for chromosome sections, individual chromosomes or even the complete chromosome set. Their number may vary dependent on the diagnostic objective from a few to several hundred target nucleic acids. The target nucleic acids may be single-stranded samples or double-stranded samples. In the latter case, the target nucleic acid must be made single-stranded by a suitable denaturization step before the CNTH test is performed. The target nucleic acids must be bound to the filter by suitable treatment of the filter so that they remain in place during the CNH procedure.

For manufacture of the CNH test matrix on glass, a procedure is required by which the target-DNA or the target-RNA is firmly bound to the glass. There are already several protocols for this purpose such as the coating of object carries with a thin polyacrylamide film and the subsequent immobilization of the samples to be applied by a process in accordance with Khrapko, et al. (Khrapko, K. R.; Lysov, Y. P.; Khorlin, A. A.; Ivanov, I. B.; Yershov, G. M.; Vasilenko,S. K.; Florentiev, V. L.; Mirzabekov,A. D.: "A METHOD FOR DNA SEQUENCING BY HYBRIDIZATION WITH OLIGO NUCLEOTIDE MATRIX". DNA-Sequence-J. DNA-Sequencing and Mapping 1:375–388, 1991). Another possibility resides in the admixing of carrier substances such as proteins which cause only few or distinguishable background signals to the target nucleic acids, the application of the mixture to the matrix and a subsequent fixing, for example by methanol/ice vinegar or formaldehyde. The selection and arrangement of the samples on the glass matrix are done as described above. Instead of glass other hard materials could be used. Microplates with preformed cavities appear to be particularly suitable.

In an alternative process for making a CNH-matrix on glass or on a filter the hybridization is performed in solution—separately for each target nucleic acid. With this method, particular attention must be given to the quantitative separation of the non-hybridized sample molecules. This can be done by conventional methods such as gelfiltration, gel-electrophoresis, chromatography or by enzymatic disintegration. The signal intensities of the test and reference-DNA are measured only after this separation. This measurement can be performed after binding of the hybridization products on a solid matrix or in solution as far as the target nucleic acids are concerned. The measurement after binding on a solid matrix is performed as described below; the measurement in solution can be performed batch-wise for each reaction batch or in an automated fashion, for example in a flow-through spectrophotometer. The signals of the test and reference nucleic acids can be determined in accordance with the signal characteristic. For example, test and reference nucleic acids can be marked by different fluorochromes. In accordance with the state of the art of fluorometry both can be excited and measured separately and, in accordance with the state of the art of the fluocytometry, they can be simultaneously excited and separately.

The marking of the nucleic acid samples by haptenes (for example, biotin or digoxigenin) or directly by fluorochromium is done by means of molecular-genetic standard procedures (for example, Nick Translation, Random Priming) as described by Lichter, P.; Cremer, T.; "CHROMOSOME ANALYSIS BY NON-ISOTOPIC IN SITU HYBRIDIZATION" in: Human Cytogenetics: "A PRACTICAL APPROACH", eds.; Rooney, D. E.; Czepulkowski, B. H.; IRL Press, Oxford: 157–192, 1992 and by Raap, A. K., Wiegert, J.; Lichter, P.; "MULTIPLE FLUORESCENCE IN SITU HYBRIDIZATION FOR MOLECULAR CYTOC;E-NETICS" in: Technics and Methods in Molecular Biology: Non-radioactive labeling and detection of bio-molecules; ed: Kessler, C.; Springer Verlag Berlin, Heidelburg, N.Y.: 343–354, 1992.

The Comparative Nucleic Acid Hybridization is performed in a way as described by Du Manoir, S.; Speicher, M. R.; Joos, S.; Schröck, E.; Popp, S.; Döhner, H.; Kovacs, G.; Robert-Nicoud, M.; Lichter, Page.; Cremer, T.: "DETECTION OF COMPLETE AND PARTIAL CHROMOSOME GAINS AND LOSSES BY COMPARATIVE GENOMIC IN SITU HYBRIDIZATION". Hum. Genet. 90:592–593, 1993 or by Speicher, M. R.; Du Manoir, S.; Schröck, E.; Holtgreve-Grez, H.; Schoell, B.; Langauer, C.; Cremer, T.;

Ried, T.: "MOLECULAR CYTOGENETIC ANALYSIS OF FORMALIN-FIXED, PARAFFIN-EMBEDDED SOLID TUMORS BY COMPARATIVE GENOMIC HYBRIDIZATION AFTER UNIVERSAL DNA AMPLIFICATION". Hum. Genet. 2: 1913–1914, 1993. The hybridization of RNA samples occurs in an analog way and under consideration of the precautions common with RNA hybridizations.

The hybridized sample sequences are detected by way of molecules which generate quantitatively determinable signals which can be sufficiently distinguished from the "background" signals of the matrix. For this purpose, fluorescent properties are preferred at this point. With fluorochromium-marked nucleic acids the sample sequences can be directly detected after the usual washing steps. Fluorescence detection reactions by haptene-marked nucleic acid samples is performed in accordance with standard procedures as described for example by Lichter, P.; Cremer, T. in: "CHROMOSOME ANALYSIS BY NON-ISOTOPIC IN SITU HYBRIDIZATION" in Human Cytogenetics: A practical approach; eds.; Rooney, D. E.; Czepulkowski, B. H.; TRL Press, Oxford: 157–192, 1992. Besides fluorescence other detection methods may be used which will provide quantifiable signals, such as chemical luminescence, phosphorescence and radioactivity in order to directly or indirectly determine the presence of nucleic acids. Different detection methods for the test and reference nucleic acids may also be combined in a single experiment.

Following the CNH procedure, the fluorescence signals are quantitatively determined for each slot of the matrix (for example, with a CCD camera) and, from that, the fluorescence quotient test nucleic acid/reference nucleic acid is calculated by a microprocessor. The fluorescence quotient is determined as described by DuManoir et al. (1993) (pages 592–593) or by Speicher et al. (1993) pages 1913–1914) with the difference that the measurements are performed with the aid of masks, not on the individual chromosomes, but within the individual target nucleic acid slots. In CNH control experiments with differently marked genomic DNA from cells with normal Karyotypes or, respectively, differently marked identical cDNA or RNA samples, the variations of these quotients which are normally to be expected are determined on the basis of a predetermined reliability level. With samples having a genomic duplication or deletion of a chromosome, of a chromosome section or of a gene which can be determined by the test, a systematic increase or, respectively, reduction of the quotient in the slots which contain the respective target nucleic acids is to be expected. The fluorescence quotient for the remaining slots however, should remain within the control range.

Since, in each slot, the hybridization signal resulting from the test genome is compared with that resulting from the normal reference DNA, the CNH matrix test should be relatively insensitive with regard to variations in the amount of target nucleic acids in the various slots which occur with the preparation of the matrix. Variations in the mixing ratio of the tumor DNA and the reference DNA as they may occur in different experiments have the same effect on all the quotients and can therefore also be standardized.

An important aspect is the selection of suitable equipment for the quantitative determination of the hybridization signals. The detection instruments should generally be capable, of measuring linear differences between the signal intensities over a wide range. For the detection of fluorescence signals various instrument configurations may be used such as: fluorescence microscopes which include a (cooled) CCD (Charged Coupled Device) camera or fluoroscanners, wherein fluorescence scanning is performed by way of an electronically controlled laser beam and detection occurs by way of a sensitive photo-multiplier. Also with the flow-through spectrophotometry excitation is obtained by a lamp or a laser and detection by way of a photomultiplier. Depending on the type of detection signals also other methods such as densitometry (see for example, phosphorous imaging) are suitable.

All measurement data should be digitally recorded and stored. The ratios of the signal intensities of test and reference nucleic acids can then be calculated utilizing suitable software.

Examples for Applications.

Important applications are in the area of clinical genetics, tumor diagnostic, clinical pathology, the analysis of animal models for genetic diseases including tumors and in breeding research.

Target nucleic acids for the matrix are selected in accordance with diagnostic requirements. If, for a particular diagnostic problem, the possible chromosomalin problems are known, a matrix with target nucleic acids can be prepared which are chosen selectively for the particular detection that is for the exclusion of these specific imbalances. (See example 3 below). For other objectives however, it is desirable to provide for as broad as possible an analysis of the genome with regard to unknown imbalances. This may be achieved for example by splitting the whole genome into a series of target nucleic acids. The resolution capability and the sensitivity of such a CNH test is then determined by the number and the genomic distribution of the target nucleic acids (see example 2 below). In order to achieve for example the resolution capability of a cytogenetic banding analysis with 400 or, respectively, 800 chromosome bands per haploidemic chromosome set each band on the matrix should be represented by a suitable target nucleic acid designated below as "400" or respectively, 800 band matrix. With such a matrix losses and gains of chromasomal regions on the so given resolution level could be determined which corresponds to the achievable resolution capability of CGH an metaphase chromosomes.

If necessary various matrices with different resolution capabilities can be sequentially tested. If for example the gain or loss of a particular chromosome segment is recognized on normal chromosomes or a 400 band matrix, in a second step a matrix can be used by which the breaking points of the imbalanced region can be more accurately determined. For this matrix, target nucleic acids are used which characterize the defined subregion of the earlier identified chromosome segment. (Example 3).

EXAMPLE 1

Screening of numerical chromosome aberrations. For this purpose, 24 target DNAs are required which represent the 24 different human chromosomes. They are combined in accordance with the diagnostic requirements (see below). The selection of target DNAs may include DNA of sorted human chromosomes; DNA of somatic hybrid cells each of which contains a human chromosome (monochromatic hybrid cells); DNA amplification products of sorted human chromosomes or monochromatic hybrid cells, pools of cloned, chromosome-specific fragments such as YACs, $P_1$-clones, cosmids or corresponding contigs of such samples. Instead of DNAs, sorted chromosomes or microorganisms which contain corresponding target nucleic acids could be directly applied to the matrix (see above).

Possible Applications a) Prenatal screening of embryonic cells for numeric changes. The most important numeric charges happen with respect to the chromosomes 13, 18, 21, X and Y. Accordingly, in this case, the matrix contains the target-DNAs of the five chromosomes referred to. If, for ethical and legal reasons, a screening of the sex chromosomes is to be excluded, then target-DNAs for only the chromosomes 13, 18 and 21 would be applied.

b) Screening for hyperploids in patients with acute lymphatic leukemia since hyperploids with n>50 have a favorable clinical prognosis. In this case it appears to be appropriate to apply target DNAs for all 24 human chromosomes.

c) Screening for tumors in which numeric aberrations play a role such as chromophobic kidney cell carcinomas or bladder carcinoma. Here too matrices to which all 24 target DNAs have been applied could be used (which would appear to be particularly suitable for bladder carcinomas) or to which target DNAs of the aberrations relevant in connection with the particular tumor entities (for example, chromophobic kidney cell carcinomas) have been applied.

EXAMPLE 2

Universal screening of unknown partial chromosome imbalances. For this, target DNAs are required which represent various sections of the human chromosomes. In analogy to present molecular-biological methods of the analysis of genomic losses ("loss of heterozygosity LOH") matrices with 42 target DNAs can be used in order to represent all the relevant chromosome arms:

1p, 1q, 2p, 2q, 3p, 3q, 4p, ,5p ,5q, 6p, 6q, 7p, 7q, 8p, 8q, 9p, 10p, 10q, 9q, 10p, 10q, 11p, 11q, 12p, 12q, 13q, 14q, 15q, 16p, 16q, 17p, 17q, 18p, 18q, 19p, 19q, 20p, 20q, 21q, 22q, Yq.

With higher resolution requirements more complex matrixes can be employed such as the "400 or 800 band matrices described above.

Possible applications:

a) Screening of patients for unknown structural chromosome aberrations b) Screening of any tumors for unknown chromosomal imbalances. This set up is important especially in the tumor biological research since, for many tumors, the diagnostically and prognostically relevant genomic imbalances are presently not identified.

EXAMPLE 3

High resolution screening of certain chromosome sections for genomic imbalances. In this case matrices are made which have target DNAs only for selected chromosome sections and which are concerned with a specific diagnostic objective.

Possible Applications:

a) For genetic counseling of families with reciprocal translations, it is important to know whether genetic imbalances have developed in the areas of the chromosomal breaking points. For such an analysis, a matrix with high resolution can be prepared which includes target DNAs which are mapped in the breaking point regions in question.

b) For a Carrier-diagnosis of x-chromosomal recessive diseases such as the Duchenne's muscular dystrophy a matrix can be prepared which contains target DNAs for sections of the respective gene.

EXAMPLE 4

Screening for genomic imbalances of tumor-relevant genes. For this, target-DNAs are required which represent well known proto-onkogenes, tumor suppressor genes or other genes which are relevant for the growth and the metastasis of a tumor.

Possible Applications:

a) The proof for the amplification of onkogenes with prognostic relevance such as N-myc amplification in the neuroblastoma.

b) The proof for the detection of tumor suppressor genes with prognostic relevance such as the deletion in 1p36 of neuroblastoma.

EXAMPLE 5

Screening for over- or under-expression of certain genes. In this connection target nucleic acids are required which contain coded sequences of selected genes. For this, in addition to the matrices described in example 4, matrices with RNAs or cDNAs of the genes may be used. As test nucleic acid, complete RNA from a cell population to be tested is isolated; as reference nucleic acid the complete RNA of a suitable control cell population with normal expression of the relevant genes may be used.

Possible applications:

With a genomic amplification of N-myo (see example 4a), a quantitative determination of the actual over-expression can be obtained with this test.

EXAMPLE 6

The examples given above for human diseases can be utilized in an analog manner for animal models with regard to the same diseases. It requires the preparation of matrices whose target nucleic acids are derived from the same species or have a conservation which is sufficiently evolutionary for the purpose of a CNH test.

Possible Applications:

In many animal models for specific tumors, it is first not known whether the basic genetic mechanism corresponds to the tumor occurring in humans. In this case, it can be expected that the results of the CNH tests for the human and the animal tumor correspond when a test is made for tumor-relevant genes (see example 4) or an expression analysis (see example 5) is performed.

EXAMPLE 7

With the preparation of transgenic organisms, CNH tests with matrices can be developed which contain target-nucleic acids of the transferred genes. With these tests, it is possible to quantitatively determine the numbers of copies of the transferred genes and the expression in the receiver organism.

Possible Applications:

a) Analysis of transgenic animals with corresponding mutated tumor relevant genes.

b) Breeding of animals and growing of plants wit changed properties.

What is claimed is:

1. In a method for the analysis of genomic variances by comparative genomic hybridization, the improvement comprising selecting, as target nucleic acid sequences for hybridization, defined subchromosomal nucleic acid sequences which are specific for gains and/or losses of genomic sequences characteristic of the cell types being screened and arranging the target nucleic acid sequences on a matrix in a specific geometric arrangement.

2. A method according to claim 1 wherein said defined subchromosomal nucleic acid sequences are selected from the group consisting of sorted chromosomes, microdissected chromosome sections, chromosomal arms, protooncogenes, tumor suppressor genes and amplified isolates from cDNA libraries.

3. A method according to claim 2 wherein said defined subchromosomal nucleic acid sequences comprise genomic sections of a few kbp up to several Mbp.

* * * * *